United States Patent
Blaine et al.

(10) Patent No.: US 12,111,105 B2
(45) Date of Patent: Oct. 8, 2024

(54) BATCH SAMPLE PREPARATION APPARATUS

(71) Applicant: REFLEX INSTRUMENTS ASIA PACIFIC PTY LTD, Balcatta (AU)

(72) Inventors: Fredrick Allan Blaine, Balcatta (AU); Amir Mokaramian, Balcatta (AU); Ben Stanley Douglas Blakeway, Balcatta (AU)

(73) Assignee: REFLEX INSTRUMENTS ASIA PACIFIC PTY LTD, Balcatta (AU)

(*) Notice: Subject to any disclaimer, the term of this patent is extended or adjusted under 35 U.S.C. 154(b) by 0 days.

(21) Appl. No.: 16/645,742

(22) PCT Filed: Sep. 13, 2018

(86) PCT No.: PCT/AU2018/051000
§ 371 (c)(1),
(2) Date: Mar. 9, 2020

(87) PCT Pub. No.: WO2019/051551
PCT Pub. Date: Mar. 21, 2019

(65) Prior Publication Data
US 2020/0284508 A1    Sep. 10, 2020

(30) Foreign Application Priority Data

Sep. 13, 2017 (AU) ................................ 2017903727

(51) Int. Cl.
*E21B 49/00* (2006.01)
*E21B 21/06* (2006.01)
(Continued)

(52) U.S. Cl.
CPC .............. *F26B 3/06* (2013.01); *E21B 21/066* (2013.01); *E21B 49/005* (2013.01);
(Continued)

(58) Field of Classification Search
CPC ............................. E21B 49/005; E21B 21/066
(Continued)

(56) References Cited

U.S. PATENT DOCUMENTS

| 5,351,894 A | 10/1994 | Longhurst et al. |
| 10,393,436 B2 * | 8/2019 | Lawie ..................... F26B 21/10 |

FOREIGN PATENT DOCUMENTS

| CN | 2849609 Y | 12/2006 |
| CN | 101354212 A | 1/2009 |

(Continued)

OTHER PUBLICATIONS

European Patent Office, Partial Supplementary European Search Report issued in corresponding Application No. 18857120.2 dated Jul. 21, 2020.
Australian Patent Office, International Search Report issued in corresponding Application No. PCT/AU2018/051000 mailed Nov. 23, 2018.
European Patent Office, Supplementary European Search Report issued in corresponding Application No. 18857120.2 dated Nov. 22, 2021.

*Primary Examiner* — Alexander A Mercado
*Assistant Examiner* — Rodney T Frank
(74) *Attorney, Agent, or Firm* — Stites & Harbison, PLLC; Terry L. Wright

(57) ABSTRACT

A batch sample preparation apparatus (10) for preparing a geological sample for analysis is described and claimed. The apparatus (10) comprises a dryer (12) having a drying chamber 52), a sample inlet (20) and at least one sample outlet (22), (24) communicating with the drying chamber (52), to a comminution device (14) in selective fluid communication via valves (26), (28) with the dryer (12) to selectively receive dried sample. The apparatus (10) has a source of fluid (74) introduced at the dryer (12) so that sample material may be transported from the dryer (12) to (Continued)

the comminution device (14) by fluid flow, which fluid flow also extracts the sample material from the comminution device (14) for collection and subsequent analysis.

17 Claims, 6 Drawing Sheets

(51) Int. Cl.
| | |
|---|---|
| *F26B 3/06* | (2006.01) |
| *F26B 3/092* | (2006.01) |
| *F26B 11/16* | (2006.01) |
| *F26B 21/04* | (2006.01) |
| *F26B 21/10* | (2006.01) |
| *G01N 1/28* | (2006.01) |
| *G01N 1/34* | (2006.01) |
| *G01N 33/24* | (2006.01) |

(52) U.S. Cl.
CPC .......... *F26B 3/0923* (2013.01); *F26B 3/0926* (2013.01); *F26B 11/16* (2013.01); *F26B 21/04* (2013.01); *F26B 21/10* (2013.01); *G01N 1/286* (2013.01); *G01N 1/34* (2013.01); *G01N 33/24* (2013.01); *G01N 2001/2866* (2013.01)

(58) Field of Classification Search
USPC ...................................................... 73/863.21
See application file for complete search history.

(56) References Cited

FOREIGN PATENT DOCUMENTS

| | | | |
|---|---|---|---|
| CN | 203298569 U | 11/2013 | |
| CN | 106766682 A | 5/2017 | |
| CN | 206478951 U | 9/2017 | |
| EP | 2594336 A1 | 5/2013 | |
| JP | 2000-197854 A | 7/2000 | |
| JP | 2012-233073 A | 11/2012 | |
| JP | 2014-181333 A | 9/2014 | |
| JP | 2014173790 A | 9/2014 | |
| KR | 100887174 B1 | 3/2009 | |
| WO | 2000/001256 A1 | 1/2000 | |
| WO | WO-0001256 A1 * | 1/2000 | ............... A23L 3/40 |
| WO | WO-2016077870 A1 * | 5/2016 | ............. F26B 1/005 |

* cited by examiner

BATCH SAMPLE PREPARATION APPARATUS

TECHNICAL FIELD

This invention relates to the preparation of samples for analysis, such as geological samples.

BACKGROUND ART

Exploration drilling involves drilling a borehole, extracting the sample and analysing the sample. In diamond drilling using a coring bit, samples are extracted in the form of a core and/or drill cuttings. In non-diamond drilling, (i.e. blast-hole drilling, reverse circulation drilling, coil-tube drilling, etc.) sample material is returned to the surface in the form of cuttings. Due to the fact that water (with or without drilling additives) is used in the drilling process to remove the cuttings as drilling progresses or the borehole may pass through one or more water tables, these cuttings are usually wet when they are returned to the surface. Water can also be used as dust suppression in drilling where air is utilized to remove the cuttings from the borehole, resulting in variably wet samples. Many other geological samples, such as soils and tills, also contain variable amounts of water and require drying.

As the moisture can interfere with the analysis (e.g. x-ray fluorescence analysis), it is therefore generally necessary to dry the sample material prior to analysis. Furthermore, depending on the type of analysis required, it may be necessary to additionally reduce the particle size of the sample material.

One of the significant disadvantages to known systems is that drying and comminution of the sample material is carried out using large dryers and crushers or mills. Large dryers of the type typically used can take several hours to dry the samples at the low temperatures required to maintain sample integrity (105° C. or lower, if volatile components are present). Therefore, there is generally a significant delay between the drilling process and the outcome of the analysis process, even in those instances where a laboratory may be established close to the drilling site.

More rapid drying techniques have been developed such as agitated infra-red drying. However, such systems are not able to prepare samples at a rate comparable to the rate at which they are produced, and are therefore not suitable for in-line drying and comminution and the type of samples that the systems can handle is limited. Also these systems are of a size and power requirement that limit the portability of these systems and they generally must be implemented in a lab or large containerized-lab environment.

Known geochemical analysis techniques may be applied to the sample material as it is returned from the borehole or sampled, but it has been found that coarse material provides poor sampling statistics and adversely affects the quality of the results obtained (for example; poor sample representivity, analytical repeatability, etc.). Many comminution techniques have been developed for the reduction of the grain-size of dry geologic material but may require multiple steps (i.e. jaw crusher followed by ring mill) and/or require partial disassembly for sample extraction or cleaning in between samples. Furthermore, comminution of variably wet material is not possible through common comminution means due to sample build-up/loss, sample carry and/or excessively cleaning required between sample batches.

In any event, the known drying and comminution systems for the scale of sample preparation required for drill cutting analysis are bulky and have not been designed to be easily transportable.

SUMMARY OF THE INVENTION

In accordance with one aspect of the present invention, there is provided a batch sample preparation apparatus for preparing a geological sample for analysis, the apparatus comprising a dryer having a drying chamber, a sample inlet and at least one sample outlet communicating with said drying chamber; said apparatus having a comminution device in selective fluid communication with said dryer to selectively receive dried sample from said at least one sample outlet; the apparatus comprising a source of fluid introduced at said dryer so that sample material may be transported from said dryer to said comminution device by fluid flow, said fluid flow also extracting the sample material from the comminution device for collection and subsequent analysis.

Preferably, said at least one sample outlet includes a fine dried sample outlet disposed at an upper region of said drying chamber and a coarse dried sample outlet disposed toward a lower region of said drying chamber.

Advantageously preferably the source of fluid comprises a source of positive fluid pressure introduced at said dryer.

The fluid may be a gas, including air.

Preferably the dryer is a fluid bed dryer comprising said source of positive fluid pressure.

Preferably said drying chamber has a sample bed having holes therein, the source of positive fluid pressure being arranged to cause fluid to flow through said holes and over said sample bed, and wherein the dryer includes agitation means located proximal to said sample bed to agitate the sample material.

The agitation means may comprise any one or more of a mechanical stirrer, PTFE balls, and ceramic balls.

Preferably said coarse dried sample outlet is located proximal to said sample bed, and a flow control valve is associated therewith to selectively control extraction of sample material through said coarse dried sample outlet.

Preferably a second sample bed is located below said sample bed between said source of positive fluid pressure and said sample bed, said second sample bed having apertures of smaller dimensions than said holes of said sample bed, said drying chamber having a third sample outlet located between said sample bed and said second sample bed with an associated flow control valve to selectively control evacuation of sub-coarse sized dried sample to said comminution device. With this arrangement, any sample that falls through the holes in the sample bed above, will be retained on the second sample bed to be entrained in fluid flow exiting via the third sample outlet.

Preferably said fine dried sample outlet includes a fines outlet flow control valve operable to maintain fluid flow in balance with operation of said flow control valve.

Preferably said apparatus further comprises at least one cyclone located downstream of said dryer, for separating sample material from the fluid.

Preferably said apparatus further includes a first cyclone disposed between said at least two sample outlets and a first inlet of the comminution device and a second cyclone disposed at an outlet of the comminution device, each cyclone having a corresponding underflow port and an overflow port.

Preferably said dryer has associated therewith, a further cyclone arranged with said drying chamber to recirculate sample to said drying chamber In this arrangement, preferably said further cyclone is provided with an eductor associated with its underflow port, to entrain sample for re-input to said drying chamber.

Preferably the apparatus further comprises a source of negative pressure associated with an overflow port of each cyclone.

Yet further, preferably the apparatus further comprises a source of negative fluid pressure disposed at an outlet to the comminution device.

The apparatus may further comprise a control inlet in fluid communication with an external environment, and a control valve for controlling fluid flow through said control inlet.

Advantageously, the control inlet may be provided on the comminution device.

Preferably the comminution device comprises an active area where the sample is crushed and wherein the airflow between the first inlet and the outlet of the comminution device transports the sample into and out of the active area.

Preferably the comminution device further comprises one or more surfaces in the active area, said surfaces acting to crush the sample, wherein the airflow between the first inlet and the outlet of the comminution device passes across at least a part of the surfaces.

Preferably the control inlet has fluid flow directed across said active area.

Preferably the comminution device is a disc mill having at least two vertical grinding discs mounted for rotation relative to a horizontal axis.

An embodiment extends to a system for preparing a geological sample for analysis, the system comprising a dryer and comminution device in fluid communication with one another, the system comprising a source of fluid pressure so that sample material may be transported between the dryer and the comminution device by fluid flow, said fluid flow also extracting the sample material from the comminution device for collection and subsequent analysis.

The fluid pressure may be positive and/or negative. In an embodiment, the fluid is air and the source of fluid pressure comprises a fan.

Embodiments of the invention may solve the problems associated with traditional approaches, allowing sample preparation (drying and comminution) and sample analysis to be done at a rate comparable to that at which the samples are generated. Furthermore, the pneumatic transfer system aids in cleaning the system allowing the system to be operated substantially as a closed system, with only periodic disassembly required for cleaning. Furthermore, embodiments of the invention may be of a size that is easily transportable in a mobile unit, thereby allowing on-site analysis to move together with the exploratory drilling rig.

An embodiment may produce samples suitable to be further analysed by the device illustrated and described in PCT application PCT/AU2015/000700.

Preferably the dryer, crusher and any cyclones are connected by fluid conduits to allow air to flow between the components. In an embodiment, the system is sealed from an external environment other than the provided inlets and outlets.

The dryer may be a fluid bed dryer. The dryer may incorporate the source of positive fluid pressure as a fan blowing air.

Sample material may be introduced into the dryer and/or comminution device in batches to allow the preparation and analysis of discreet samples. Cross contamination between samples may be avoided.

The comminution device may comprise a disk mill. The disk mill may comprise at least two vertical grinding disks, with at least one horizontal axis of rotation. A distance between the two vertical grinding discs may be variable.

The system may further comprise at least one cyclone for separating sample material from the fluid.

The system may comprise two cyclones, a first cyclone disposed between the dryer and the comminution device and a second cyclone disposed at an outlet of the comminution device. Each cyclone may have a corresponding underflow port and an overflow port.

The overflow ports of one or both cyclones may be associated with a source of negative pressure. During operation, the cyclones may provide a positive pressure at the respective underflow ports.

The system may further comprise a control inlet in fluid communication with an external environment, and a control valve for controlling fluid flow through said control inlet. By controlling the amount of external air entering the system, negative and positive pressures may be balanced. Preferably, the control inlet is disposed downstream of the source of positive pressure and the first cyclone.

By matching the negative pressure associated with the first cyclone to the positive pressure provided by the fluid bed dryer (which includes the source of positive pressure) to thereby produce a relatively small positive pressure at the underflow of the first cyclone, the portion of the system upstream from the first inlet to the comminution device can be decoupled from the portion of the system downstream of the comminution device. This may allow the first cyclone to operate more efficiently, and facilitates regulation of fluid flow through the comminution device. The system may further comprise a source of negative pressure disposed at an outlet to the comminution device. Combined with the slight positive upstream pressure provided by the first cyclone this may generate airflow through the comminution device. This may allow the comminution device to be cleaned simultaneously with transporting sample material there through.

The comminution device may comprise an active area where the sample is comminuted and wherein the airflow between the first inlet and the outlet of the comminution device transports the sample into and out of the active area.

The comminution device may further comprise one or more surfaces in the active area, said surfaces acting to comminute the sample, wherein the airflow between the first inlet and the outlet of the comminution device passes the surfaces.

The control inlet, as herein defined, may be provided on the comminution device. By providing the control inlet on the comminution device, the control inlet may be operated to clean the comminution device in addition to balancing the positive and negative pressures in the system.

A further embodiment extends to a dryer for preparing a geological sample for analysis comprising a housing enclosing a sample bed, the dryer further comprising a source of fluid pressure to cause fluid to flow over the sample bed, the housing having a sample inlet for introducing sample material and at least one sample outlet for extracting dried sample material, wherein the sample inlet, housing and sample outlet are arranged so that sample material may be extracted from the dryer through the sample outlet by fluid flow wherein the dryer includes means for agitating the sample material.

The dryer may further comprise a heating element arranged so that the fluid is heated prior to flowing over the sample bed. In an embodiment, the fluid is air.

In an embodiment, the sample material has a range of particle sizes from less than 10 μm to 25 mm. It should however be evident that the apparatuses can be scaled to accommodate larger particle sizes. Sample material may have varying moisture levels up to the point of a free-flowing liquid phase. In the circumstances, existing drying methods are less effective since the fine fractions are cohesive and do not separate into individual particles or small enough agglomerates to provide the surface area required for efficient drying.

Since embodiments incorporate convective drying and fluid bed drying together with agitation, which prevents fine material forming large agglomerates, the drying times may be significantly reduced. Furthermore, the agitation may provide the added advantage of cleaning the dryer.

The dryer may dry the sample material to a moisture content of less than 5% by weight. The dryer may dry the sample to a moisture content of less than 1% by weight.

The agitation means may comprise any one or more of a stirrer, PTFE (Teflon) balls and ceramic balls. In a further embodiment the agitation means may comprise a vibratory motor or other means to vibrate the sample bed.

The dryer may include multiple sample outlets, wherein fine-grained sample material is extracted through a first sample outlet and coarse-grained sample material is extracted through a second sample outlet. The first sample outlet may be an upper sample outlet and the second sample outlet may be a lower sample outlet. Finer sample material may be extracted from the upper sample outlet and coarser sample material from the lower sample outlet.

The agitation means may be loose. The lower sample outlet may be provided with a screen to prevent loose agitation means from being extracted together with the coarse sample material. In a further embodiment, the lower outlet and loose agitation means are dimensioned so that the loose agitation means cannot pass through the lower outlet.

In another embodiment the lower sample outlet may comprise a vertical tube extending to the base of the drying chamber, with or without a rotating vacuum nozzle to extract the coarse material out of the top of the unit.

The dryer may further comprise a thermostat and/or manual temperature control. Preferably, the thermostat regulates a temperature of the dryer to 95 degrees centigrade, or less. In an embodiment, the temperature may be less than 105 degrees centrigrade.

The system as herein described may comprise a dryer as herein described.

The first and second outlets of the dryer may feed into a feeder port of a first cyclone.

A further embodiment extends to a method of preparing a geological sample for analysis, the method comprising:
   drying the geological sample to form a dried geological sample;
   generating a fluid flow to transport the dried geological sample to a comminution device; and
   comminuting the dried geological sample material in the comminution device.

The fluid may be a gas.

The fluid flow may be generated by positive pressure.

The fluid flow may additionally be generated by negative pressure and the method may further comprise balancing the positive and negative pressures.

The method may further comprise using a fluid bed dryer to dry the geological sample and to generate the positive fluid pressure.

The method may further comprise drying and/or comminuting the geological sample in batches.

The method may further comprise separating sample material from the fluid using at least one cyclone.

The method may further comprise disposing a first cyclone between the dryer and the comminution device and a second cyclone at an outlet of the comminution device.

The method may further comprise disposing a source of negative fluid pressure at an overflow port of the first cyclone.

The method may further comprise using a control inlet in fluid communication with an external environment to balance pressures.

The comminution device may comprise an active area where the sample is comminuted and wherein the method further comprises using the airflow between the inlet and the outlet of the comminution device to transport the sample into and out of the active area.

The comminution device may further comprise one or more surfaces in the active area, said method further comprising crushing the sample using said surfaces and wherein the airflow between the inlet and the outlet of the comminution device passes the surfaces.

In an embodiment, the method comprises the further step of analysing the sample using X-ray diffraction or X-ray fluorescence. Similarly, the system hereinbefore described may further comprise an X-ray diffraction instrument and/or an X-ray fluorescence instrument.

A further embodiment of the invention extends to a comminution device for preparing a geological sample for analysis, the comminution device comprising a housing enclosing an active area where the sample is comminuted, the housing further comprising a first inlet and an outlet, wherein sample material may be introduced into the housing via the first inlet, and extracted from the housing via the outlet, wherein the housing is sealed to allow fluid flow between the first inlet and the outlet to thereby transport sample material through the active area by means of the fluid flow.

The housing may further comprise a control inlet connecting an interior of the housing to an external environment and a valve for controlling fluid flow into the housing via the control inlet. Operation of the valve may vary an amount of air entering the housing. This may assist in cleaning of the comminution device.

The comminution device may further comprise one or more surfaces in the active area, said surfaces acting to comminute the sample material.

The comminution device may comprise a disc mill having at least two vertical grinding discs mounted for rotation relative to a horizontal axis.

BRIEF DESCRIPTION OF THE DRAWINGS

Notwithstanding any other forms which may fall within the scope of the system and method as set forth in the Summary, specific preferred embodiments will now be described by way of example only with reference to the accompanying drawings in which.

DETAILED DESCRIPTION OF SPECIFIC EMBODIMENTS

FIG. 1 is a schematic drawing of apparatus 10 for preparing a batch geological sample according to the first embodiment of the invention. The apparatus 10 comprises a dryer 12 and a comminution device in the form of a disc mill 14 which are connected pneumatically via a first cyclone 16, in order that pressurised air may transfer sample material between the dryer 12 and the disc mill 14.

Figure 3A:
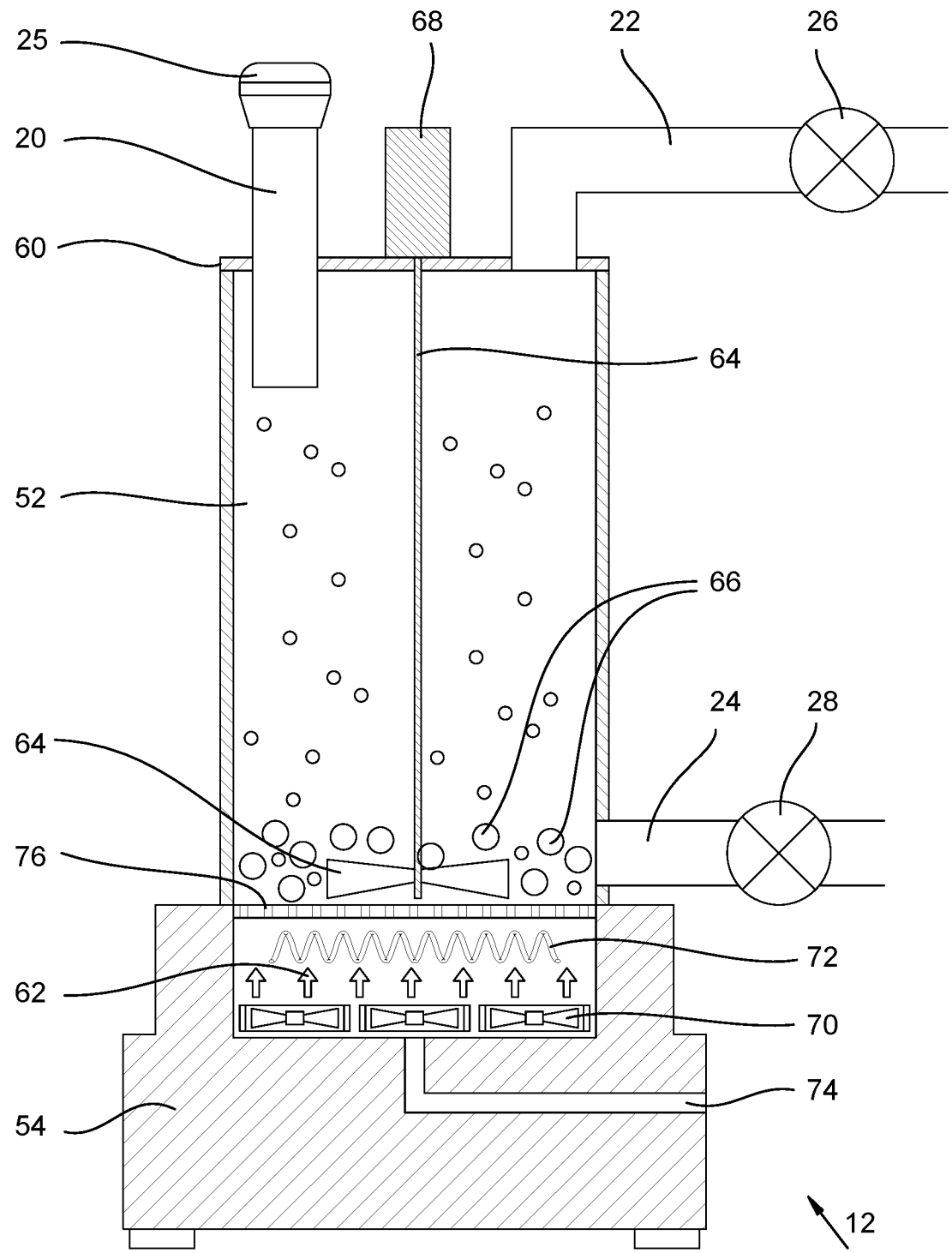
FIG. 3A is a cross-section of the dryer of FIG. 2.

Referring also to FIG. 3A, the dryer 12 includes an inlet 20 into which sample material is introduced, and two outlets 22 and 24 which combine and transport sample material to the dryer 12 via the first cyclone 16 disposed between the dryer 12 and the disc mill 14. The inlet 20 is provided with a sealing closure 25 to seal the inlet 20 once the sample material has been introduced into the dryer 12. Flow control valves 26 and 28 disposed within outlets 22 and 24 respectively, to control the outputs of the dryer. In this embodiment the sample material is introduced into the inlet 20 manually. In an alternative embodiment, the sample material may be introduced into the inlet 20 automatically, e.g. by means of an automated conveyor system.

As described in greater detail below with reference to FIGS. 2 and 3, the dryer 12 is a fluid bed dryer and accelerated hot air is introduced into the apparatus 10 by the dryer 12. This hot air creates a positive pressure which helps to transport the sample material pneumatically through the apparatus 10, when the either or both flow control valves 26 and 28 are opened.

Referring back to FIG. 1A, a vacuum pump 36 is connected by conduit 34 to the overflow port 37 of the first cyclone 16. A feeder port 33 of the cyclone 16 is, in turn, attached to the outlets 22 and 24 of the dryer 12. Therefore, air flow occurs between the source of air flow, being the dryer 12, and the vacuum pump 36, attached to the overflow port 37 of the cyclone 16.

Conduit 30 is attached to an underflow port 35 of the cyclone 16 and to the disc mill 14. The disc mill 14 is connected by conduit 32 to the inlet port 41 of the second cyclone 18. An underflow port 43 of the second cyclone 18 is connected to conduit 42 provided with a flow control valve 44, which can be opened in order to deliver dried and comminuted sample from the disc mill 14.

Vacuum pump 40 is connected via conduit 38 to an overflow port 39 of the second cyclone 18.

Prepared samples are delivered via output conduit 42 controlled by flow control valve 44.

The first cyclone 16 and second cyclone 18 may be configured with or without vortex breakers, as required, and with sample collection facilities, as required.

Figure 1A:
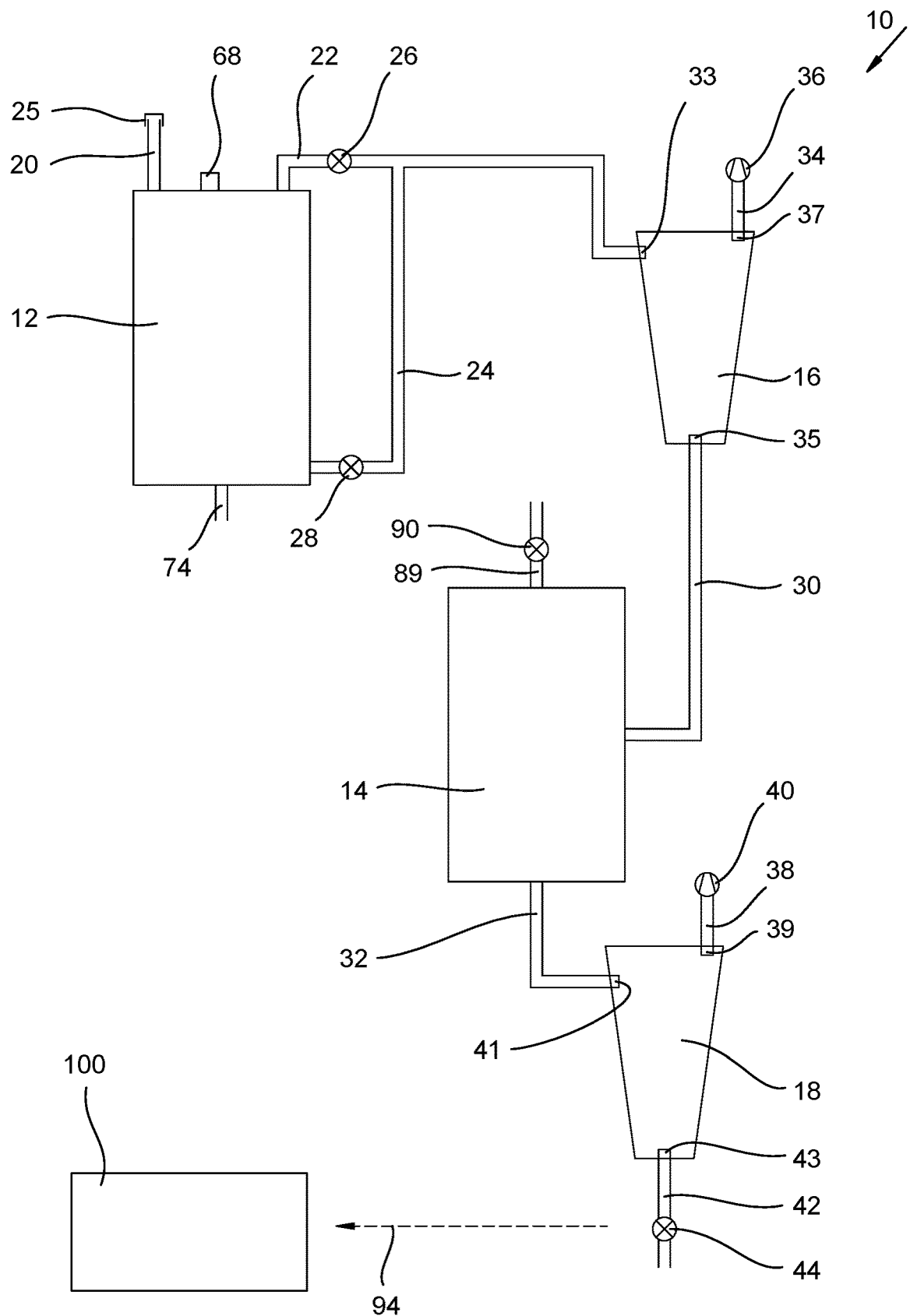
FIG. 1A is a schematic drawing of apparatus for preparing a geological sample according to a first embodiment of the invention.
Figure 2:
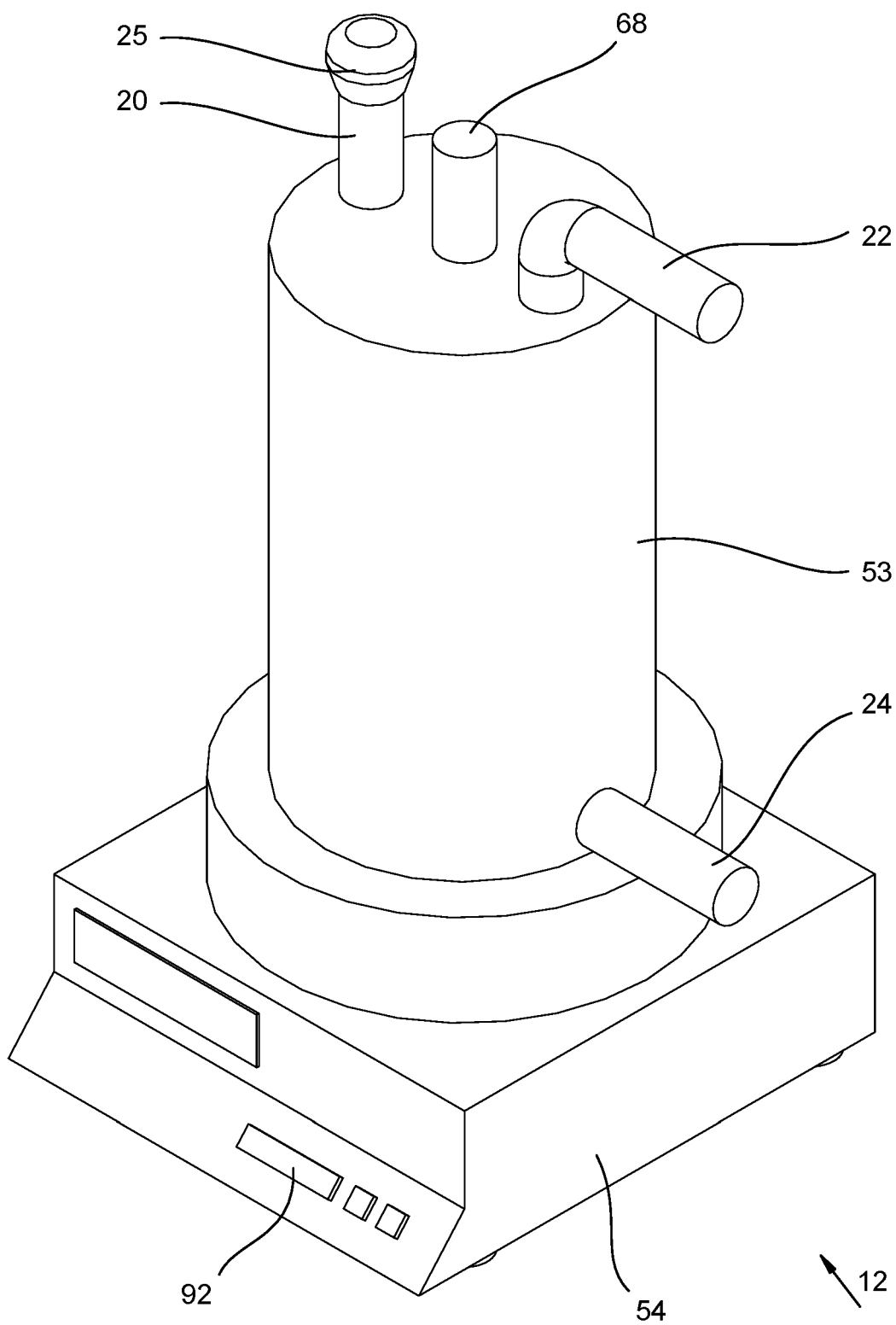
FIG. 2 is a perspective view of a dryer utilised in the first embodiment of the invention.

FIG. 2 illustrates a perspective view of the dryer 12 used in the apparatus 10 illustrated in FIG. 1A. The dryer 12 comprises a housing 53. Inlet 20 provides an inlet through which sample material is introduced into the dryer 12.

Furthermore, the dryer 12 includes two sample outlets, a top sample outlet 22 and a bottom sample outlet 24, from the housing 53.

In another embodiment the second sample outlet comprises a vertical tube extending toward the base of the dryer 12 to extract the coarse material out of the top of the unit. In an alternative arrangement, the vertical tube is provided with a rotating vacuum nozzle.

The details of the dryer 12 are apparent from the cross-section of FIG. 3. As illustrated there, the housing 53 defines a drying chamber 52 which is sealed from the environment by a removable lid 60 and the sealing closure 25. Although not illustrated in this Figure, the dryer may further include a clamp to seal the lid 62. In an embodiment, sealing the chamber of the dryer from the environment helps to assist pneumatic transfer of the sample material, as well as potentially improving the efficiency of the drying process.

An air inlet 74, provided at the bottom of the dryer, is connected to fans 70. A heating element 72 is disposed between the fans 70 and a sample bed 76. The sample bed 76 has a plurality of spaced holes formed therein which are advantageously sized at 50 µm, but this may be varied depending on the nature of the sample. The holes in the sample bed are arranged so as to form a mesh-like structure in the sample bed 76, allowing the passage of air therethrough, across the horizontal surface of the sample bed 76, from the underside of the sample bed 76 to the top side thereof. When the fans 70 are operational, air is drawn in through the air inlet 74, past the heating element 72 where it is heated, and enters into the drying chamber 52 as shown by arrows 62, through the holes in the sample bed 76. Sample material which is introduced through inlet 20 will interact with the warm air thereby helping to dry the sample material.

A stirrer 64 is disposed along a central axis of the chamber 52 and is driven by a stirrer motor 68. In this embodiment, the stirrer comprises a PTFE (Teflon) or aluminium paddle which is located just above the sample bed 76, but it is to be realised that in other embodiments, a stirrer with a different composition or configuration may be used. It may be important in embodiments of the invention that the stirrer is able to withstand the temperatures provided in the drying chamber 52.

In this embodiment, the stirrer motor 68 rotates the stirrer 64 at the speed between 30 and 180 rpm. It is to be realised that the speed of the stirrer motor will depend on the volume of the drying chamber 52, the characteristics of the sample material being introduced, the dimensions of the stirrer etc.

In the embodiment illustrated in FIG. 3, ceramic balls 66 are provided within the drying chamber 52. In an alternative embodiment, the balls 66 are made from PTFE (Teflon). Ceramic and PTFE may have an advantage that these materials do not interact with the sample material. Other inert materials may be used to produce appropriate sample agitation.

In embodiments of the disclosed system, the agitation and the fluid effects from the hot air entering in through the sample bed 76 act to dry the sample material in a number of different ways:

Fine material breaks up through the action of the agitating media and dries and is transported out of the system.

Moderately-sized material forms a fluidized bed and is agitated by the action of the stirrer 64 and the balls 66 as well as the fluidizing effect of the hot air.

Coarse material is agitated by the stirrer 64 and the balls 66, which cause it to dry efficiently.

As illustrated in FIG. 2, the dryer 12 includes a manual temperature control 92 which allows a user to adjust the temperature of the hot gas used by the fluid bed dryer. This may be useful to ensure that the temperature which the sample material exposed to does not affect any volatiles in the sample material. In an alternative embodiment, a thermostat is provided to regulate the temperature of the gas. The temperature in the chamber 52 may be kept at 95 degrees centigrade, or less.

Figure 4:
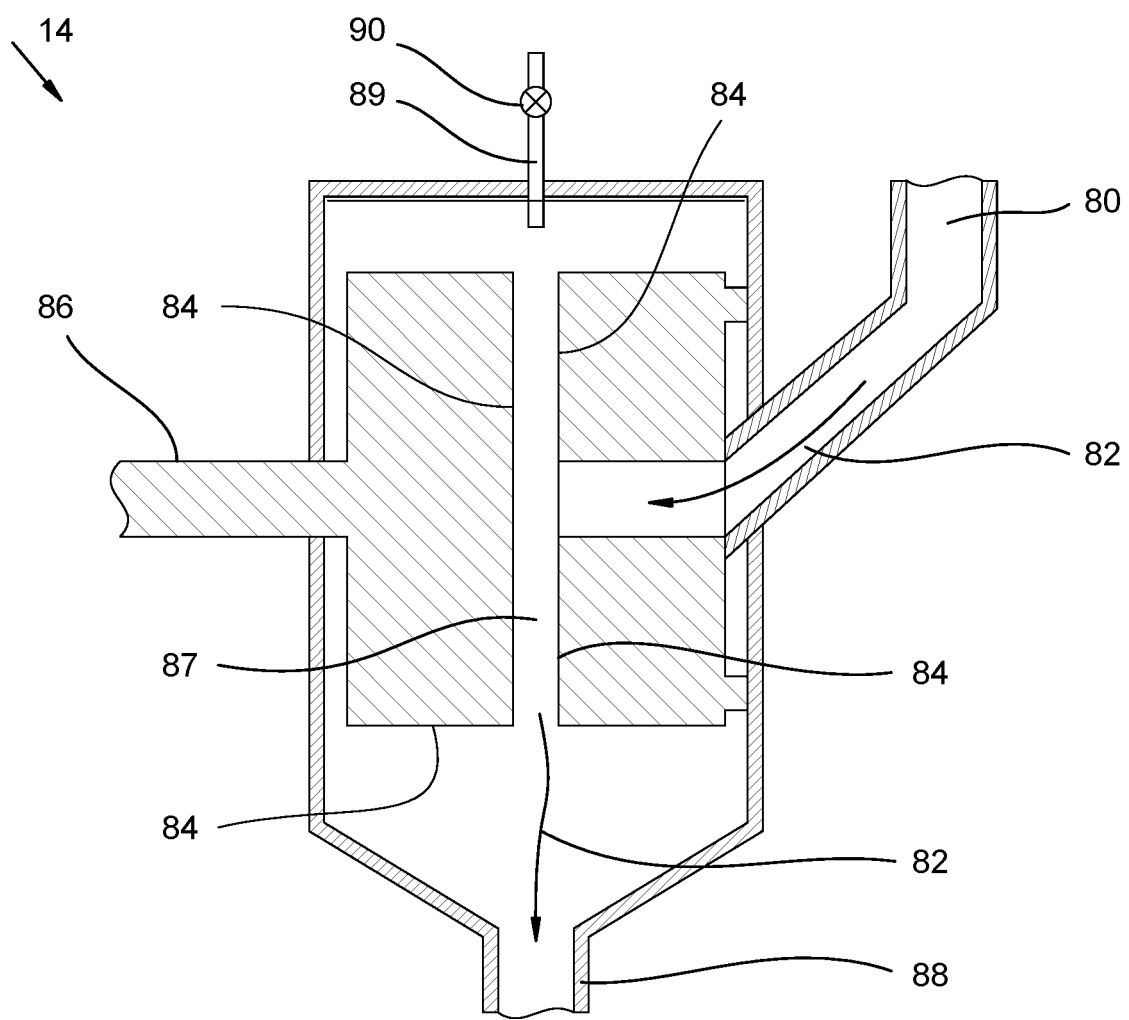
FIG. 4 is a cross-section of a comminution device utilised in all three embodiments of the invention.

The disc mill 14 is illustrated in greater detail in FIG. 4. The disc mill 14 includes an inlet 80 attached to the conduit 30 illustrated in FIG. 1. Sample material is introduced into the disc mill 14 by the airflow, the direction of which is illustrated by arrows 82. The disc mill includes two grinding discs 84 spaced apart by a distance which is adjustable by a screw thread 86 to vary the action of the disc mill 14.

In this embodiment, the area between the grinding discs 84 of the disc mill 14 forms an active area 87 in so far as the sample is crushed in this area. Advantageously, the airflow between the inlet 80 and the outlet 88 of the disc mill transports sample material into and out of the active area. The airflow has the added advantage of providing a cleaning action to the grinding discs 84. In this embodiment, the surfaces of the grinding discs 84 act to crush the sample material.

The disc mill 14 further comprises a control inlet 89 connecting the interior of the disc mill to the outside environment. A variable control valve 90 is disposed on the control inlet 89 and controls the amount of air flowing through the control valve 90, to augment the airflow from inlet 80, and promote material transfer from the disc mill 14 out the outlet 88 thereof, and to promote cleaning of the disc mill 14. In this embodiment, the variable control valve 90 is a manual valve, but in alternate embodiments automatic or electronic control may be exerted over this valve.

The sample material will exit the disc mill, borne by the airflow depicted by arrows 82, through the outlet 88 which is attached to the conduit 42 illustrated in FIG. 1.

The operation of the system 10 illustrated in FIG. 1A will now be described.

Sample material is introduced into the inlet 20 in batches. As illustrated in FIG. 3, the sample material enters the dryer 12 through the inlet 20 and the hot air produced by the fans 70 and heating element 72, together with the agitation provided by the stirrer 64 and the ceramic balls 66 dries and disperses the sample material.

The dryer comprises an upper sample outlet 22 and a lower sample outlet 24; finer sample material may be extracted from the upper sample outlet 22 and coarser sample material from the lower sample outlet 24. The flow control valve at the upper sample outlet may be opened in order to promote flow through of air from air inlet 74. As the sample is dried, finer sample material will be entrained in the flow through the upper sample outlet 22 where it progresses through the apparatus 10. Coarser sample may take a longer time to dry, and when it is determined that the coarser sample is sufficiently dried, the flow control valve 28 can be opened to evacuate dried sample from the region above the sample bed 76, via the lower sample outlet 24. The flow control valve 26 may be throttled back to alter the flow balance to increase flow through the lower sample outlet.

The lower sample outlet is provided with a screen such as a wire mesh or grate (not shown) to prevent agitation means such as balls from being extracted together with the coarse sample material. Alternatively, in a further embodiment, the lower outlet and balls are dimensioned so that the balls cannot pass through the lower outlet.

Since the dryer 12 provides a positive air pressure, operation of the respective valves 26 or 28 allows the sample material to pass through and enter cyclone 16. Furthermore, the vacuum source 36 connected by conduit 34 to cyclone 16 provides a negative pressure at the valves 26 and 28.

The first cyclone 16 acts in a known manner to collect and aggregate the sample material. The sample material is then passed through conduit 30 to the disc mill 14. The sample material is drawn through the disc mill 14 through the action of the negative pressure provided by vacuum source 40 connected to the second cyclone 18 (see below).

The sample material is crushed between grinding discs 84. Since finer material will pass through the gap between the discs 84 unaffected, the disc mill tends to produce sample material with a more consistent particle size. Sample material is extracted from the disc mill 14 through outlet 88 and enters second cyclone 18 by means of conduit 32. The cyclone 18 acts to collect the sample material in a known manner.

The vacuum provided at the cyclone 16 augments the flow of the sample material through the dryer 12. Furthermore, the movement of air through the disc mill, past the grinding discs 84, may advantageously provide cleaning action, removing sample material from any particular batch.

Together, the dryer 12 and first cyclone 16 with associated vacuum pump 36 form a first pneumatic transfer system. Second cyclone 18 and associated vacuum pump 40 together with disk mill 14 form a second pneumatic transfer system.

Operation of the control valve 90 disposed in the control inlet 89 varies the amount of air from the outside which enters the disc mill 14. This will affect the pressure in the entire system since the disc mill is in fluid communication with the dryer 12 and cyclones 16 and 18 (and their associated vacuum pumps). Therefore the control valve helps to set and regulate the pressure in the system 10 of FIG. 1.

The pressures may, for example, be set to prevent the conduit 30 between the cyclone and the disk mill 14 from being pressurized, i.e. air is drawn through the grinding discs 84 of the disc mill 14 by the vacuum associated with the second cyclone 18, and not pushed through the grinding discs by the positive pressure provided by the dryer 12. This may allow the first cyclone 16 to operate efficiently by allowing a decoupling between the first and second pneumatic transfer systems, so that positive pressures and vacuums may not have to be balanced exactly.

It is to be realised that the control valve 90 may be disposed elsewhere in the system 10 and still provide the function of setting the pressures and allowing balancing of various positive and negative pressures. Providing the control valve 90 on the disc mill has the added advantage that by opening and closing the control valve, sample material from one batch may be cleared from the disc mill prior to introduction of sample material from the next batch.

Once the material has been collected by the second cyclone 18, it exits via conduit 42 controlled by flow control valve 44.

In embodiments of the disclosed system and method, the collected sample may be produced in a time period comparable to that at which sample material is being produced by the drill or other extraction method.

As illustrated and discussed above, sample material is transferred through the system 10 by airflow and therefore the system is largely sealed from the environment.

As mentioned above, sample material is processed in batches, controlled by the manner in which the material is introduced into the dryer via inlet 20, extracted from the dryer 12 via the outlets 22 and 24, and by the operation of the variable control valve 90 of the comminution device 14.

This sample may then be transferred for further analysis. As illustrated in FIG. 1, sample material in powder form is transferred from the system 10 to an X-ray diffraction instrument 100 (as illustrated by dashed arrow 94).

In a further embodiment, a puck of sample material may be formed in an intermediate step and transferred to an X-ray fluorescence instrument. In an embodiment, the X-ray diffraction instrument and/or X-ray fluorescence instrument form part of the system 10.

Figure 1B:
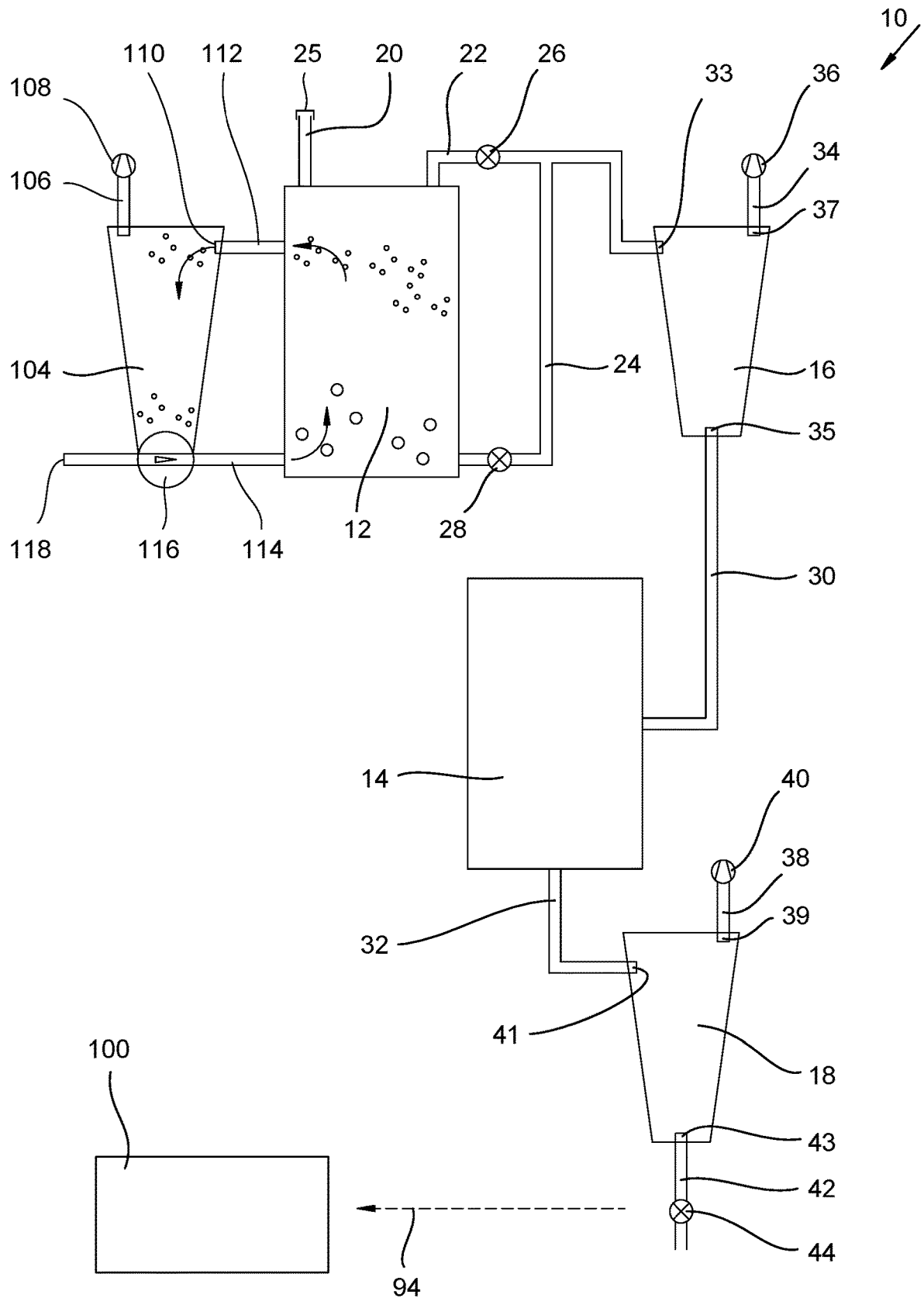
FIG. 1B is a schematic drawing of apparatus for preparing a geological sample according to a second embodiment of the invention.

Referring to FIG. 1B, the second embodiment of the batch sample preparation apparatus is illustrated. In this second embodiment, like numbers illustrate features described in apparatus according to the first embodiment, and their function is the same. The second embodiment differs in that associated with the dryer 12 is a further cyclone 104 having an overflow port 106 connected with a vacuum source 108. The cyclone 104 has an input 110 connected with a pipe 112 which receives sample entrained in air, drawn by the vacuum source 108, from the drying chamber 52. The sample is separated from the flowing air within the cyclone 104 and selectively returned via pipe 114 to the drying chamber 52 of the dryer 12 by an eductor 116. An inlet pipe 118 provides a source of positive air pressure to operate the eductor 116 to entrain the sample separated by the cyclone 104, and overcome the pressure within the drying chamber 52 to return the sample to the drying chamber 52. Operation of the cyclone 104 with the dryer 12 is carried out with both flow control valves 26 and 28 closed, isolating the drying stage from the comminution stage.

The effect of the cyclone 104 and eductor 116 is to recirculate sample to the dryer and effectively increase the residence time of the sample at the drying stage. This ensures that the sample can be thoroughly dried as a complete sample (and not separated into fine and coarse streams), before it is transferred for comminution. This also decouples the drying stage from the comminution stage, allowing a previously dried batch sample to be comminuted while a fresh sample is being dried.

Figure 3B:
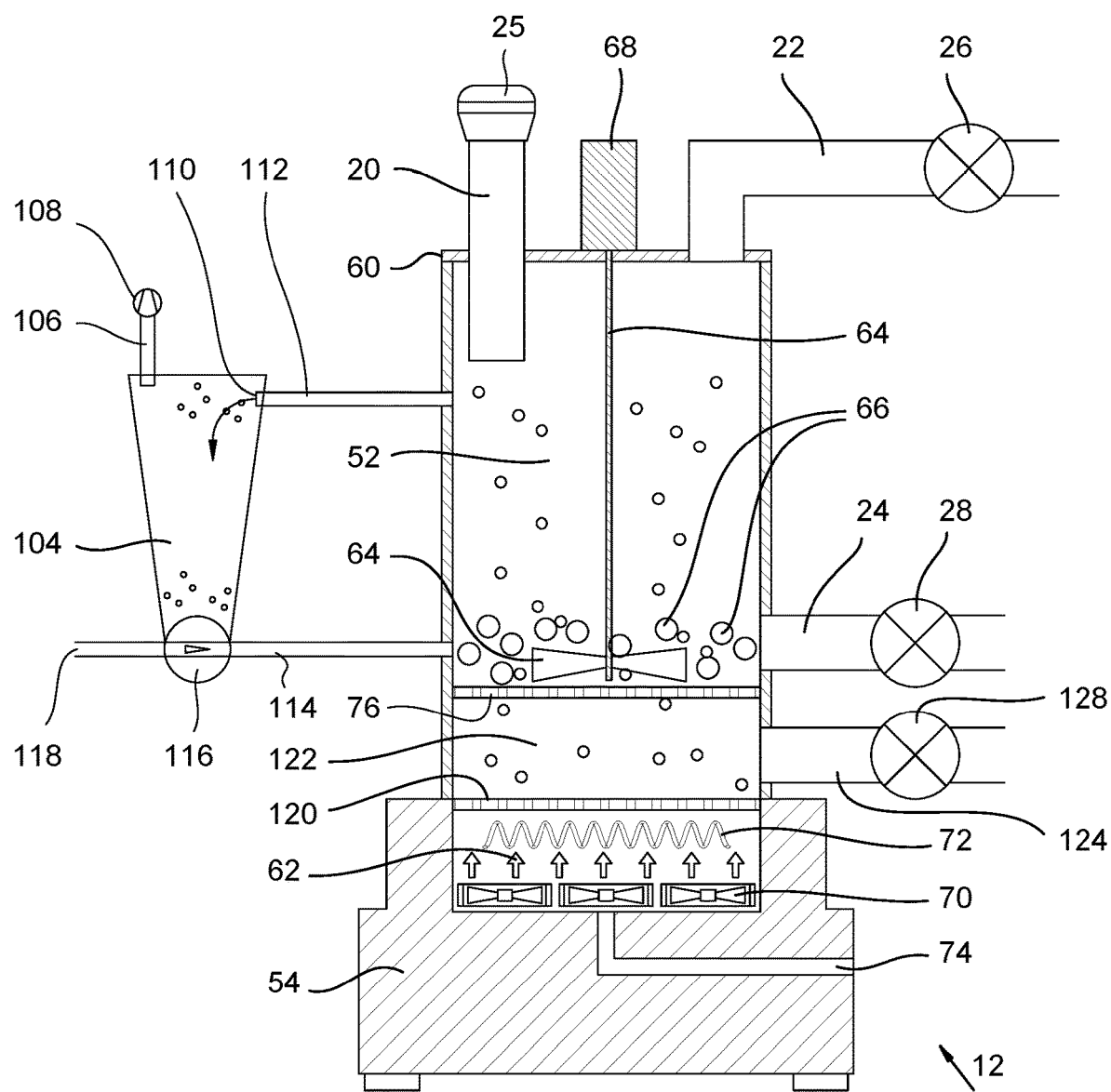
FIG. 3B is a cross-section of a dryer utilised in a third embodiment of the invention.

Referring to FIG. 3B, the dryer 12 used in the third embodiment of the batch sample preparation apparatus is illustrated. In this third embodiment, like numbers illustrate features described in apparatus according to the first two embodiments, and their function is the same. The third embodiment utilises the circuit with the drying chamber formed by the cyclone 104 and eductor 116 to increase mean residence time of the sample in the drying chamber 52.

The dryer 12 of the third embodiment differs from that of the first two embodiments in that the sample bed 76 and agitator 64 are raised, and a second sample bed 120 is provided located below the sample bed 76, between the sample bed 76 and the heating element 72. This embodiment features coarser holes, nominally of 500 μm, in the sample bed 76, which provides a stronger sample bed 76 able to withstand stronger agitation, than the sample beds in the first two embodiments. The second sample bed 120 has apertures that are finer than the holes in the sample bed 76, nominally being of size 25 μm, to collect any fine sample that falls though the holes in the sample bed 76. The sample bed 120 with finer apertures will not be as strong as the sample bed 76, but this is of no consequence since the second sample bed will not be under as much mechanical stress, not having an agitator contacting coarse sample in contact with it, as the sample bed 76 has. The apertures in the sample bed 120 are spread evenly across the sample bed 120 so as to form a mesh structure to retain any ground sample that falls from above, while allowing passage of air from the underside of the sample bed 120 to the top side of the sample bed. Since there is not the same mechanical stress placed on the lower sample bed 120, the sample bed may be of a finer mesh than the sample bed 76 of any of the embodiments. A void 122 is provided between the sample bed 76 and the second sample bed 120. A third sample outlet in the form of a further outlet port 124 with an associated flow control valve 128 is provided communicating with the space between the sample bed 76 and the second sample bed 120, the outlet of the flow control valve 128 connecting with the feeder port 33 of the cyclone 16, joining the outlets of flow control valves 26 and 28. Operation of the dryer of the third embodiment is the same as that of the second embodiment, except that fine sample that falls through the holes in the sample bed 76 into the space between the sample bed 76 and the second sample bed 120, will be retained above the second sample bed 120, on account of the apertures in the second sample bed 120 being finer than the holes in the sample bed 76. Periodic operation of the flow control valve 128 allows evacuation of sub-coarse sized sample that has fallen into the space between the sample bed 76 and the second sample bed 120, to the cyclone 16.

A further fourth embodiment of the dryer 12 within the apparatus 10 is envisaged, where the dryer 12 has the two sample beds 76 and 120 and ducts 22, 24 and 124 as described in the third embodiment, but does not have the circuit with the drying chamber formed by the cyclone 104 and eductor 116 utilised in the second and third embodiments.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be understood to persons skilled in the art of the invention that many modifications may be made without departing from the spirit and scope of the invention.

The invention claimed is:

1. A batch sample preparation apparatus for preparing a geological sample for analysis, the apparatus comprising:
    a dryer having a drying chamber, a sample inlet, a fine dried sample outlet disposed at an upper region of said drying chamber, and a coarse dried sample outlet disposed toward a lower region of said drying chamber;
    a comminution device in selective fluid communication with said dryer to selectively receive dried sample from said fine dried sample outlet and/or said coarse dried sample outlet, the comminution device for milling, crushing, and/or grinding the dried sample;
    a first cyclone disposed between said sample outlets and a first inlet of the comminution device, and a second cyclone disposed at an outlet of the comminution device, each cyclone having a corresponding underflow port and an overflow port; and
    a source of fluid introduced at said dryer so that sample material may be transported from said dryer to said comminution device by fluid flow;

wherein the comminution device includes a control inlet arranged in fluid communication with an external environment, and having a control valve for controlling fluid flow through said control inlet for setting and facilitating pressure balancing between the dryer and comminution device, whereby opening and closing of said control valve allows clearing of sample material from the comminution device prior to introduction of sample material from a following batch, and whereby fluid flow also extracts the sample material from the comminution device for collection and subsequent analysis.

2. Apparatus according to claim 1 wherein the source of fluid comprises a source of positive fluid pressure introduced at said dryer.

3. Apparatus according to claim 1 wherein the fluid is a gas.

4. Apparatus according to claim 2 wherein the dryer is a fluid bed dryer comprising said source of positive fluid pressure.

5. Apparatus according to claim 4 wherein said drying chamber has a sample bed having holes therein, the source of positive fluid pressure being arranged to cause fluid to flow through said holes and over said sample bed, and wherein the dryer includes agitation means located proximal to said sample bed to agitate the sample material.

6. Apparatus according to claim 5 wherein the agitation means comprises any one or more of a mechanical stirrer, PTFE balls, and ceramic balls.

7. Apparatus according to claim 5 wherein said coarse dried sample outlet is located proximal to said sample bed, and a flow control valve is associated therewith to selectively control extraction of sample material through said coarse dried sample outlet.

8. Apparatus according to claim 7 wherein a second sample bed is located below said sample bed between said source of positive fluid pressure and said sample bed, said second sample bed having apertures of smaller dimensions than said holes of said sample bed, said drying chamber having a third sample outlet located between said sample bed and said second sample bed with an associated flow control valve to selectively control evacuation of sub-coarse sized dried sample to said comminution device.

9. Apparatus according to claim 2 wherein said fine dried sample outlet includes a fines outlet flow control valve operable to maintain fluid flow in balance with operation of said flow control valve.

10. Apparatus according to claim 1 wherein said dryer has associated therewith, a further cyclone arranged with said drying chamber to recirculate sample to said drying chamber.

11. Apparatus according to claim 9 wherein said further cyclone is provided with an eductor associated with its underflow port, to entrain sample for re-input to said drying chamber.

12. Apparatus according to claim 9 further comprising a source of negative pressure associated with an overflow port of each cyclone.

13. Apparatus according to claim 1 further comprising a source of negative fluid pressure disposed at an outlet to the comminution device.

14. Apparatus according to claim 1 wherein the comminution device comprises an active area where the sample is crushed and wherein the airflow between the first inlet and the outlet of the comminution device transports the sample into and out of the active area.

15. Apparatus according to claim 14 wherein the comminution device further comprises one or more surfaces in the active area, said surfaces acting to crush the sample, wherein the airflow between the first inlet and the outlet of the comminution device passes across at least a part of the surfaces.

16. Apparatus according to claim 15 wherein the control inlet has fluid flow directed across said active area.

17. Apparatus according to claim 1 wherein the comminution device is a disc mill having at least two vertical grinding discs mounted for rotation relative to a horizontal axis.

* * * * *